United States Patent
Buchanan et al.

(10) Patent No.: US 7,115,538 B2
(45) Date of Patent: Oct. 3, 2006

(54) ETHYLBENZENE CONVERSION CATALYST AND PROCESS

(75) Inventors: John Scott Buchanan, Lambertville, NJ (US); Robert A. Crane, Hellertown, PA (US); Doron Levin, Annandale, NJ (US); Daria N. Lissy, Glen Mills, PA (US); Gary D. Mohr, Houston, TX (US); David L. Stern, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 490 days.

(21) Appl. No.: 10/309,634

(22) Filed: Dec. 4, 2002

(65) Prior Publication Data

US 2004/0214713 A1    Oct. 28, 2004

Related U.S. Application Data

(60) Provisional application No. 60/336,652, filed on Dec. 5, 2001.

(51) Int. Cl.
*B01J 29/87*    (2006.01)
*B01J 29/06*    (2006.01)

(52) U.S. Cl. .............. 502/60; 502/64; 502/66; 502/74; 502/77

(58) Field of Classification Search .......... 502/64, 502/66, 60, 74, 77
See application file for complete search history.

(56) References Cited

U.S. PATENT DOCUMENTS

| | | | |
|---|---|---|---|
| RE31,919 E | 6/1985 | Butter et al. .............. 502/66 |
| 4,849,385 A * | 7/1989 | Huang et al. .............. 502/35 |
| 4,899,011 A | 2/1990 | Chu et al. ................ 585/481 |
| 4,952,543 A * | 8/1990 | Huang et al. .............. 502/35 |
| 5,188,996 A * | 2/1993 | Huang et al. .............. 502/37 |
| 5,689,027 A | 11/1997 | Abichandani et al. ...... 585/481 |
| 2002/0107139 A1* | 8/2002 | Degnan et al. ............ 502/177 |

* cited by examiner

*Primary Examiner*—Elizabeth D. Wood
(74) *Attorney, Agent, or Firm*—Xiaobing Feng

(57) ABSTRACT

An ethylbenzene conversion catalyst is described which comprises a molecular sieve and a hydrogenation metal, wherein the catalyst exhibits a benzene hydrogenation activity at 100° C. of less than about 100 and a metal dispersion, as measured by hydrogen chemisorption, greater than 0.4 and wherein the molecular sieve is steamed to an alpha value of less than 400 prior to incorporation of the palladium with the molecular sieve.

9 Claims, No Drawings

ETHYLBENZENE CONVERSION CATALYST AND PROCESS

CROSS REFERENCE TO RELATED APPLICATIONS

This application claims priority to U.S. Provisional Patent Application No. 60/336,652, filed Dec. 5, 2001.

FIELD

This invention is directed to an ethylbenzene conversion catalyst and process and in particular to a catalyst and process for effecting the ethylbenzene conversion stage of a multi-stage xylene isomerization process.

BACKGROUND

Para-xylene is a valuable chemical feedstock, which may be derived from mixtures of $C_8$ aromatics separated from such raw materials as petroleum naphthas, particularly reformates, usually by selective solvent extraction. The $C_8$ aromatic fractions from these sources vary quite widely in composition but will usually comprise 10 to 32 wt % ethylbenzene (EB) with the balance, xylenes, being divided between approximately 50 wt % of the meta isomer and 25 wt. % each of the para and ortho isomers.

Individual isomer products may be separated from the naturally occurring mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization, selective adsorption (e.g., the Parex process), or membrane separation.

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability to convert ethylbenzene in the feed to useful by-products while simultaneously minimizing any conversion of xylenes to other compounds.

One commercially successful xylene isomerization process is described in U.S. Pat. No. 4,899,011 in which a $C_8$ aromatic feed, which has been depleted in its para-xylene content, is contacted with a two component catalyst system. The first catalyst component selectively converts the ethylbenzene by deethylation, while the second component selectively isomerizes the xylenes to increase the para-xylene content to a value at or approaching the thermal equilibrium value. The first catalyst component comprises a Constraint Index 1–12 zeolite, which has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury, whereas the second component comprises a Constraint Index 1–12 zeolite which has an ortho-xylene sorption time of less than 10 minutes under the same conditions. In one preferred embodiment, the first catalyst component is ZSM-5 having a crystal size of at least 1 micron and the second catalyst component is ZSM-5 having a crystal size of 0.02–0.05 micron. Each catalyst component also contains a hydrogenation metal, preferably a noble metal such as platinum or palladium.

An improvement over the process of U.S. Pat. No. 4,899,011 is described in U.S. Pat. No. 5,689,027 in which the first catalyst component in the two component system is pre-selectivated by coking, or more preferably by deposition of a surface coating of silica, to increase its ortho-xylene sorption time to greater than 1200 minutes under the same test conditions as cited in the '011 patent. Using such a system it is found that high ethylbenzene conversion rates can be achieved with significantly lower xylene losses than obtained with the process of the '011 patent. Again, the catalyst components employed in the process of the '027 patent include a hydrogenation metal, preferably a noble metal such as platinum, palladium, iridium, rhenium, osmium or ruthenium.

One method of producing the noble metal-containing zeolite catalysts employed in the processes of the '011 patent and the '027 patent is disclosed in U.S. Pat. Reissue No. 31,919 and involves incorporating the noble metal in cationic form with the zeolite after zeolite crystallization but before final catalyst particle formation and before any calcination or steaming of the zeolite. Where the noble metal is platinum, the Examples in the '919 patent demonstrate improved ethylbenzene conversion with relatively low xylene loss.

Despite recent advances reported above, there remains an ongoing need to provide an ethylbenzene conversion catalyst that achieves even lower xylene losses especially without the pre-sulfiding step normally employed to reduce the aromatics saturation activity of the catalyst. Thus, for example, although platinum-containing catalysts are effective for ethylene saturation, they also catalyze aromatic ring saturation, particularly at low temperatures, which typically requires pre-sulfiding of the catalyst or operation at elevated temperature, even though the latter produces adverse effects on product slates and/or cycle lengths.

SUMMARY

Accordingly, the invention resides in one aspect in an ethylbenzene conversion catalyst comprising a molecular sieve and a hydrogenation metal, wherein said catalyst exhibits a benzene hydrogenation activity at 100° C. of less than about 100 and a metal dispersion, as measured by hydrogen chemisorption, greater than 0.4 and wherein said molecular sieve has been steamed to an alpha value of less than 400 prior to incorporation of the hydrogenation metal with the molecular sieve.

Conveniently, said catalyst exhibits a benzene hydrogenation activity at 100° C. of less than about 30 and a metal dispersion, as measured by hydrogen chemisorption, of at least 0.5.

Preferably, said molecular sieve has been steamed to an alpha value of about 50 to about 250 prior to incorporation of the hydrogenation metal with the molecular sieve.

In one embodiment, said hydrogenation metal is palladium, typically such that said catalyst contains about 0.01 to about 1 wt % of palladium.

Conveniently, said hydrogenation metal is not sulfided.

Conveniently, said molecular sieve has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury.

In a further aspect the invention resides in a process for converting ethylbenzene in a feed containing ethylbenzene and xylenes comprising the step of contacting the feed in the presence of hydrogen and under ethylbenzene conversion conditions with an ethylbenzene conversion catalyst comprising a molecular sieve and a hydrogenation metal, wherein said catalyst exhibits a benzene hydrogenation activity at 100° C. of less than about 100 and a metal dispersion, as measured by hydrogen chemisorption, greater than 0.4 and wherein said molecular sieve has been steamed to an alpha value of less than 400 prior to incorporation of the hydrogenation metal with the molecular sieve.

In yet a further aspect, the invention resides in a process for isomerizing a feed, which contains ethylbenzene and xylene, which process comprises the steps of:

(a) contacting the feed in the presence of hydrogen and under ethylbenzene conversion conditions with an ethylbenzene conversion catalyst comprising a molecular sieve and a hydrogenation metal, wherein said catalyst exhibits a benzene hydrogenation activity at 100° C. of less than about 100 and a metal dispersion, as measured by hydrogen chemisorption, greater than 0.4 and wherein said molecular sieve has been steamed to an alpha value of less than 400 prior to incorporation of the hydrogenation metal with the molecular sieve; and (b) contacting the ethylbenzene-depleted effluent from step (a) with a xylene isomerization catalyst under xylene isomerization conditions.

Conveniently, the xylene isomerization catalyst comprises a molecular sieve having a Constraint Index of about 1 to about 12 combined with a hydrogenation metal.

Conveniently, the molecular sieve of the xylene isomerization catalyst has an alpha value of less than about 50 and also has an ortho-xylene sorption time of less than 50 minutes, and more preferably less than 10 minutes, based on its capacity to sorb 30% of the equilibrium capacity of ortho-xylene at 120° C. and an ortho-xylene partial pressure of 4.5±0.8 mm of mercury.

In one embodiment, the hydrogenation metal of the xylene isomerization catalyst is palladium.

Conveniently, the molecular sieve of the ethylbenzene conversion catalyst has an average crystal size in excess of 0.1 micron and the molecular sieve of the xylene isomerization catalyst has an average crystal size less than 0.1 micron.

DETAILED DESCRIPTION OF THE EMBODIMENTS

The present invention is directed to a catalyst and process for converting high percentages of the ethylbenzene present in mixed ethylbenzene-xylene containing feeds, while simultaneously minimizing xylene loss and converting xylenes to approximately the thermal equilibrium concentration. In this way, the volume of any recycle stream and/or complexity of the separation processes needed in a xylene recovery process are minimized.

One typical mode of ethylbenzene (EB) reduction is generally through transalkylation to benzene (BZ) and diethylbenzene (DEB). A representation of this reaction is given below:

EB+EB→BZ+DEB    (1)

Another typical reaction for EB reduction is through dealkylation to BZ and ethylene (ETH). A representation of this reaction is given below:

EB→BZ+ETH    (2)

The ethylene produced is very reactive and is quickly saturated to ethane using hydrogen in the presence of a hydrogenation metal. Several undesirable side reactions may also take place, leading to xylene (XYL) loss. Representations for some of the major side reactions are given below:

EB+XYL→BZ+DMEB    (3)

EB+XYL→TOL+MEB    (4)

XYL+XYL→TOL+TMB    (5)

ETH+XYL→DMEB    (6)

where: DMEB is dimethylethylbenzene, TOL is toluene and MEB is methylethylbenzene.

In the process of this invention, any reaction leading to ethylbenzene destruction or conversion is referred to herein as "ethylbenzene conversion". Of these reactions, reactions as depicted by equations 1 and 2 are desirable. Reactions as depicted in equations 3 through 6 along with similar and related types of reaction are undesirable and are collectively referred to as reactions leading to xylene loss.

An additional reaction, which occurs in the presence of the hydrogenation metal, is ring saturation which of course also leads to xylene loss. Hence in practice, there is a tension between the need to effect rapid conversion of ethylene resulting form EB dealkylation and the need to avoid ring saturation.

According to the invention, it has now been found that a metal-containing molecular sieve catalyst with excellent ethylbenzene conversion activity and extremely low xylene loss can be produced, without the need for pre-sulfiding, by tailoring the catalyst such that it has a benzene hydrogenation activity at 100° C. of less than about 100 and a metal dispersion, as measured by hydrogen chemisorption, greater than 0.4.

Feedstock

In general, any aromatic $C_8$ mixture containing ethylbenzene and xylene may be used as feed to the process of this invention. Generally, such a mixture will typically have an ethylbenzene content in the approximate range of 5 to 60 weight percent, an ortho-xylene content in the approximate range of 0 to 35 weight percent, a meta-xylene content in the approximate range of 20 to 95 weight percent and a para-xylene range of about 0 to 15 weight percent. In one embodiment, the feed may contain about 8 to 15 wt. % ethylbenzene In addition to the above aromatic $C_8$ mixture, the feed may contain non-aromatic hydrocarbons, i.e., naphthenes and paraffins, in an amount up to about 30 weight percent. The present catalyst may have high activity for cracking of normal and branched paraffins of the type present in commercial unextracted $C_8$ aromatic streams.

In one embodiment, the invention provides means to process a mixture of $C_8$ aromatics such as that derived from catalytic reforming of a petroleum naphtha to a mixture of reduced ethylbenzene content and increased content of para-xylene. The process of the invention is particularly effective in treating a para-xylene lean mixture of $C_8$ aromatics to increase the para-xylene concentration up to approximately the thermal equilibrium level.

Catalyst System

The catalyst system used in the present invention includes a first ethylbenzene conversion catalyst and, preferably, a second xylene isomerization catalyst. As their names suggest, the first catalyst has the primary function of selectively converting the ethylbenzene in the feedstream, preferably by dealkylation, to benzene and $C_2$ components, while the second catalyst component selectively isomerizes xylenes in the feed. The first catalyst component can, and preferably will, effect some isomerization of the xylenes in the feed.

Each of the first and second catalyst components comprises a molecular sieve and a hydrogenation metal or metal compound.

In one embodiment, the molecular sieve of each of the first and second catalyst components is an intermediate pore size molecular sieve having Constraint Index of about 1 to about 12 (e.g., having a pore size less than about 7 Angstroms, such as from about 5 to less than 7 Angstroms). The method by which Constraint Index is determined is described fully in U.S. Pat. No. 4,016,218, incorporated herein by reference for details of the method. Suitable intermediate pore size molecular sieves are those having the structure types MFI, MEL, MTW, TON, MTT FER and MFS using the designations adopted by the IUPAC Commission on Zeolite Nomenclature. Conveniently, the molecular sieves are aluminosilicate forms having a silica/alumina molar ratio of at least 12. Examples of intermediate pore size molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449; ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780), with ZSM-5 being particularly preferred. The entire contents of the above patents are incorporated by reference herein.

The molecular sieve of each of the first and second catalyst components also contains a hydrogenation metal. Examples of suitable hydrogenation metals include Group 8 metals (i.e., Pt, Pd, Ir, Rh, Os, Ru, Ni, Co and Fe), Group 6 metals (i.e, Cr, Mo, W), Group 14 metals (i.e., Sn and Pb), Group 15 metals (i.e., Sb and Bi), and Group 7 metals (i.e., Mn, Tc and Re). In one embodiment, the hydrogenation metal, particularly of the ethylbenzene conversion component, is a noble metal (i.e., Pt, Pd, Ir, Rh, Os and Ru), particularly is palladium. It is to be appreciated that the hydrogenation metal is not necessarily present on the catalyst in the free metal (i.e., zero valent) form, but can also be present as a compound, such as an oxide, hydroxide or sulfide, of the metal. The metal is typically in a reduced valence state, e.g., when this component is in the form of an oxide or hydroxide. The reduced valence state of the metal may be attained, in situ, during the course of a reaction, when a reducing agent, such as hydrogen, is included in the feed to the reaction.

The hydrogenation metal may be incorporated into the catalyst by methods known in the art, such as ion exchange, impregnation or physical admixture. For example, solutions of appropriate metal salts may be contacted with the remaining catalyst components under conditions sufficient to combine the respective components. The metal containing salt is preferably water soluble. Examples of such salts include chloroplatinic acid, platinum chloride and tetraammineplatinum and tetraamminepalladium complexes. After incorporation of the metal, the catalyst is calcined at a temperature of from about 250 to about 500° C.

The amount of the hydrogenation-dehydrogenation metal is suitably from about 0.001 to about 10 percent by weight, e.g., from about 0.1 to about 5 percent by weight, e.g, from about 0.1 to about 2 percent by weight, although this will, of course, vary with the nature of the component, with less of the highly active noble metals being required than of the less active base metals. Where the hydrogenation metal is palladium, the amount present is suitably from about 0.01 to about 1 wt % of the overall catalyst.

In practicing the process of the invention, it may be desirable to formulate either or both of the first and second catalyst components with another material resistant to the temperature and other conditions of the process. Such matrix materials include inorganic oxide materials such as clays, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components can also be used. In addition, the molecular sieve can be composited with a zeolitic matrix material using the method described in International Patent Publication No. WO96/16004, the entire contents of which are incorporated herein by reference.

The relative proportions of molecular sieve component and inorganic oxide matrix on an anhydrous basis may vary widely with the molecular sieve content ranging from between about 1 to about 99 percent by weight and more usually in the range of about 10 to about 80 percent by weight of the dry composite.

The first and second components of the catalyst system of the invention differ from each other in a number of significant respects which ensure that first component selectively deethylates the ethylbenzene in the feedstream to benzene while the second component selectively isomerizes xylenes in the feed. These differing characteristics are discussed below.

For example, each of the components of the catalyst system of the invention will normally exhibit mutually exclusive xylene diffusional properties. These properties can be identified by noting the time (in minutes) required to sorb 30% of the equilibrium capacity of ortho-xylene at 120° C. and at an ortho-xylene partial pressure of 4.5±0.8 mm of mercury, a test described in U.S. Pat. Nos. 4,117,026; 4,159,282; and Re. 31,782; each of which is incorporated by reference herein. The equilibrium capacity of ortho-xylene is defined herein as greater than 1 gram of xylene(s) per 100 grams of molecular sieve. In the catalyst system of the invention, the first catalyst component effective for ethylbenzene conversion conveniently has an ortho-xylene sorption time (in minutes) in excess of about 50, such as greater than about 1200, but less than 10,000, minutes, while on the other hand, the second, isomerization component conveniently has an ortho-xylene sorption time of less than about 50 minutes such as less than about 10 minutes.

Ethylbenzene Conversion Component

The first catalyst component, which selectively deethylates the ethylbenzene in the feedstream to benzene, is selected such that it exhibits a benzene hydrogenation activity at 100° C. of less than about 100 and a metal dispersion, as measured by hydrogen chemisorption, greater than 0.4. In one embodiment, the first catalyst component is selected such that it exhibits a benzene hydrogenation activity (BHA) at 100° C. of less than about 30 and a hydrogen chemisorption value of at least 0.5.

As used herein, the benzene hydrogenation activity (BHA) of a particular catalyst is the zero order rate constant for the hydrogenation activity of the catalyst for benzene at atmospheric pressure and 100° C. The BHA value is defined as the number of moles of benzene converted per mole of hydrogenation metal on the catalyst per second. The BHA values referred to herein are determined at atmospheric pressure over a fixed bed of a catalyst sample at a hydrogen to benzene molar ratio of 200:1 and a WHSV based on benzene of 500 hr$^{-1}$. Prior to contacting the catalyst sample with the benzene/hydrogen mixture, the sample is purged with helium at room temperature. Hydrogen is then introduced and the temperature is raised to 110° C. and held for one hour, then raised to 250° C. and held for another hour to fully reduce the hydrogenation metal. After the catalyst cools to 25° C., the benzene/hydrogen mixture is introduced and then the temperature is progressively raised from 50° C. to 75° C., then to 100° C. and finally to 125° C. Conversion measurements are made at each temperature and an Arrhenius plot is generated and used to determine the rate constant at 100° C.

As used herein, the hydrogen chemisorption value of a particular catalyst is a measure of metal dispersion on the catalyst and is defined as the ratio of the number of moles of atomic hydrogen sorbed by the catalyst to the number of moles of hydrogenation metal contained by the catalyst. The hydrogen chemisorption values referred to herein are measured using the following technique. Helium is first flowed over the catalyst sample to remove water. Next, hydrogen is flowed over the sample at 350° C. for 30 minutes. This is followed by a helium purge, then evacuation at or near the temperature of reduction for 1 hour. Finally, the sample is cooled in vacuum to the chemisorption temperature (35° C.). The adsorbate gas, hydrogen, is dosed in, and after equilibration, the pressure indicates the amount of gas present (assuming ideal gas). The difference between what was expected (no adsorption) and what is measured, gives the adsorption. This process is repeated until an isotherm has been generated. Extrapolation of the linear region to zero pressure gives the chemisorption value.

The catalyst is provided with the required combination BHA and hydrogen chemisorption values by selecting palladium as the hydrogenation metal and steaming the catalyst to an alpha value of less than 400, and preferably to an alpha value of about 50 to about 250, prior to incorporating the palladium on the catalyst.

Alpha value is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

Steaming to lower the alpha value of the catalyst to the values described above is typically achieved by heating the catalyst at a temperature of from about 100° C. to about 600° C., e.g., from about 175° C. to about 325° C., in an atmosphere containing from about 1% to about 100% steam, e.g., from about 50% to about 100% steam, at a pressure of from about 0.01 psia to about 50 psia (70 Pa to 345 kPa), for a duration of about 0.1 to about twenty-four hours, e.g., from about three to about six hours.

As previously stated, the ethylbenzene conversion catalyst conveniently has an ortho-xylene sorption time in excess of about 50 minutes and such as greater than about 1200, but less than 10,000, minutes. The desired xylene diffusion properties can be achieved in a number of ways. For ortho-xylene diffusion times at or near the minimum value of 50 minutes, the selection of a large crystal form of the molecular sieve used in the catalyst, that is having an average crystal size in excess of 1 micron, may be sufficient. However, to achieve higher diffusivity values, it may be desirable to selectivate the first catalyst component by deposition on the surface of the catalyst particles of a layer of coke and/or an oxide, such as silica, which is inert under the process conditions experienced in use. Where the catalyst particles are selectivated, both large crystal size and medium crystal size (having a crystal size of 0.2–0.5 micron) molecular sieves can be used in the first catalyst component.

Where the first catalyst component is to be selectivated with silica, this is conveniently achieved by subjecting the catalyst to one or more treatments with an organosilicon compound in a liquid carrier, each treatment being followed by calcination of the treated material in an oxygen-containing atmosphere, e.g., air. Such a multiple selectivation procedure is described in U.S. Pat. No. 5,476,823, the entire contents of which are incorporated herein by reference. Where the catalyst to be silica-selectivated includes a binder, it is preferable to employ a non-acidic binder, such as silica.

The organosilicon compound, which is used to selectivate the first catalyst component may, for example, be a silicone, a siloxane, a silane or mixture thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselection silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetra-siloxane. Mixtures of these compounds may also be used as preselectivating agents, as may silicones with other functional groups.

Typically, the kinetic diameter of the organosilicon compound, that is used to preselectivate the molecular sieve, is larger than the molecular sieve pore diameter, in order to avoid entry of the organosilicon compound into the molecular sieve pores and any concomitant reduction in the internal activity of the molecular sieve.

Suitable organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

The liquid carrier for the organosilicon compound may be an organic compound, such as a linear, branched or cyclic hydrocarbon having five or more, especially 7 or more, carbon atoms per molecule, e.g., an alkane, such as heptane, octane, nonane or undecane. The boiling point of the organic compound, e.g., alkane, may be greater than about 70° C. Mixtures of low volatility organic compounds, such as hydrocracker recycle oil, may be employed as carriers. Suitable organic carriers are decane and dodecane.

Following each impregnation with the organosilicon compound, the catalyst is calcined at a rate of from about 0.2° C./minute to about 5° C./minute to a temperature greater than 200° C., but below the temperature at which the crystallinity of the molecular sieve is adversely affected. This calcination temperature will generally be below 600° C. and preferably is within the approximate range of 350 to 550° C. The duration of calcination at the calcination temperature may be from 1 to 24 hours, e.g., from 2 to 6 hours.

In addition to, or in place of, silica selectivation, the first catalyst component may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. This contact temperature may be, for example, less than about 650° C. Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. No. 4,117,026, incorporated by reference herein. By using a combination of silica selectivation followed by coke selectivation, the number of organosilicon impregnation treatments required to achieve a particular xylene diffusivity can be reduced.

The ethylbenzene conversion catalyst may be in the form of particles having a surface to volume ratio of about 80 to <200 inch$^{-1}$, preferably about 100 to 150 inch$^{-1}$. Thus it has now been found that the ethylbenzene conversion reaction is sensitive to intraparticle (macroporous) diffusion limitations. By selecting the shape and size of the particles of the catalyst such that the surface to volume ratio is within the specified range, it is found that the intraparticle diffusion distance can be decreased without excessively increasing the pressure drop across the first catalyst bed. This assists in reducing the xylene losses accompanying the ethylbenzene conversion in the first catalyst bed, while at the same time increasing the xylene isomerization activity of the catalyst. Producing an ethylbenzene conversion catalyst with the desired surface to volume ratio can readily be achieved by controlling the particle size of the catalyst or by using a shaped catalyst particle, such as the grooved cylindrical extrudate described in U.S. Pat. No. 4,328,130 or a hollow or solid polylobal extrudate as described in U.S. Pat. No. 4,441,990, the entire contents of both of which are incorporated herein by reference. For example, a cylindrical catalyst particle having a diameter of $\frac{1}{32}$ inch and a length of $\frac{3}{32}$ inch has a surface to volume ratio of 141, whereas a quadralobed solid extrudate having the external shape disclosed in FIG. 4 of U.S. Pat. No. 4,441,990 and having a maximum cross-sectional dimension of $\frac{1}{16}$ inch and a length of $\frac{3}{16}$ inch has a surface to volume ratio of 128. A hollow tubular extrudate having an external diameter of $\frac{1}{10}$ inch, an internal diameter of $\frac{1}{30}$ inch and a length of $\frac{3}{10}$ inch has a surface to volume ratio of 136.

In addition, the first catalyst component may have enhanced macroporosity achieved by adding a thermally decomposable organic material to the mix used to extrude the catalyst particles and then calcining the extruded particles to remove the organic material. The thermally decomposable organic material can be any material which is compatible with the extrudable mix used to form the catalyst particles and which is retained within the mass of the extruded catalyst particles but which can be removed from the catalyst particles by heating to leave macroporous voids within the particles. A suitable organic material is a cellulose such as that sold under the trade name Avicel.

Isomerization Component

The second component of the catalyst system is effective to isomerize the xylenes of the feed containing $C_8$ aromatics. The second, isomerization component conveniently has an ortho-xylene sorption time of less than about 50 minutes, such as less than about 10 minutes. This is typically achieved by using a small crystal size molecular sieve, having an average crystal size of 0.02–0.05 micron, in this component. The molecular sieve of the second component of the catalyst system will typically have an alpha value less than about 50, such as from about 5 to about 25. The second component of the catalyst system may be prepared with the use of a thermally decomposable organic material so as to increase its macroporosity. In addition, the size and shape of the particles of the second catalyst component can be selected so as to have a surface to volume ratio of about 80 to <200 inch$^{-1}$, preferably about 100 to 150 inch$^{-1}$.

Process Conditions

The conditions used in the process of the invention are not narrowly defined, but generally will include a temperature of from about 400 to about 1,000° F. (204 to 540° C.), a pressure of from about 0 to about 1,000 psig (100 to 7000 kPa), a weight hourly space velocity (WHSV) of between about 0.1 and about 200 hr$^{-1}$, and a hydrogen, $H_2$, to hydrocarbon, HC, molar ratio of between about 0.2 and about 10. Typical conditions include a temperature of from about 650 to about 850° F. (343 to 454° C.), a pressure of from about 50 and about 400 psig (445 to 2860 kPa), a WHSV of between about 3 and about 50 hr$^{-1}$ and a $H_2$ to HC molar ratio of between about 1 and about 5.

In general, the process of the invention is carried out in a fixed bed reactor containing the catalyst system described above. In one embodiment, the first and second components of the catalyst system are located in sequential beds in a single reactor. That is, the component of the catalyst system used in the process of the invention, which is effective for ethylbenzene conversion, forms a first bed, while the other component of the catalyst system, which is effective for xylene isomerization, forms a second bed downstream of the first bed. The feed is suitably cascaded from the first to the second bed without intervening separation of light gases. As an alternative, the first and second beds could be disposed in separate reactors, which, if desired, could be operated at different process conditions. Additional catalyst beds may be provided prior to or after the first and second catalyst components of the invention.

After the conversion process, the isomerization product can be treated to isolate para-xylene and/or other desirable xylene(s). Thus, for example, the isomerizate product can be fed to a variety of para-xylene recovery units, such as a crystallizer, a membrane separation unit, or a selective adsorption unit, and thus the para-xylene may be isolated and recovered. The residual isomerizate can be stripped of products lighter than $C_8$. Products heavier than $C_8$ in the residual isomerizate can be further processed or may be fractionated out. $C_8$ fractions from which para-xylene has been removed can be recycled to the isomerizer.

One result of the process of this invention is to convert the mixed xylene components of the feed containing para-xylene in an amount less than that at thermal equilibrium to an extent such that product from the isomerizer contains para-xylene in an amount at least approaching that at thermal equilibrium.

Another result of the process of this invention is the conversion of a high proportion of the ethylbenzene contained in the mixed xylene feed with minimal xylene loss. For example, ethylbenzene conversion levels of greater than 50wt % can be accomplished at xylene loss levels of less than 2 wt %. Moreover, the use of palladium as the hydrogenation metal avoids the need for presulfiding and also suppresses the undesirable hydrogenolysis reactions that can occur if the hydrogen co-feed contains alkane and/or alkene impurities. The invention will now be more particularly described with reference to the accompanying Examples.

EXAMPLE 1

ZSM-5 (having a crystal size of about 1 micron) and $Al_2O_3$ were extruded to 1/20" quadralobe shaped particles and dried at 250° F. (120° C.) to produce a material with 50:50 by weight ZSM-5:$Al_2O_3$. This material was then precalcined in nitrogen at 1000° F. (540° C.) for three hours, then exchanged with ammonium nitrate, calcined in air at 1000° F. (540° C.) for 6 hours and then steamed at 875° F. (468° C.) for 3 hours. Finally, the material was impregnated with tetraammine palladium nitrate by incipient wetness and calcined at 975° F. (524° C.) for 1 hour to produce a catalyst containing 0.1 wt % Pd. The resultant material had an alpha value of 138, a BHA of 23 and a palladium dispersion, as measured by hydrogen chemisorption, of 0.53.

EXAMPLE 2 (COMPARATIVE)

A 50:50 by weight ZSM-5/$Al_2O_3$ 1/16 inch diameter, cylindrical extrudate, in which the ZSM-5 had a crystal size of about 1 micron, was impregnated with tetraammine palladium chloride solution by incipient wetness, dried at 250° F. (120° C.), and calcined at 660° F. (349° C.) in air for 3 hours to give a catalyst with an alpha value of 160 and 0.12% Pd. The catalyst was then steamed in 100% steam at 900° F. (482° C.) for 3½ hours to reduce acid activity. The final alpha value of this catalyst was 75 and its BHA was 8.

EXAMPLE 3 (COMPARATIVE)

ZSM-5 (having a crystal size of about 1 micron), $Al_2O_3$, and tetraammine palladium nitrate were extruded to 1/20" quadralobe shaped particles and dried at 250° F. (120° C.) to produce a material with 50:50 by weight ZSM-5:$Al_2O_3$ and 0.1 wt % Pd. This material was then precalcined in nitrogen at 1000° F. (540° C.) for three hours, then exchanged with ammonium nitrate and calcined in air at 1000° F. (540° C.) for 6 hours. Finally, the material was steamed at 875° F. (468° C.) for 3 hours to lower the alpha value of the catalyst to 164. The final catalyst had a BHA value of 11 and a palladium dispersion, as measured by chemisorption, of 0.39.

EXAMPLE 4

The catalyst of Example 3 (Catalyst A) and the catalyst of Example 1 (Catalyst B) were evaluated for use in the conversion of ethylbenzene in a microunit at 743° F. (395° C.), 20 WHSV, 1:1 $H_2$:HC, and 120 psi (827 kPa) $H_2$ partial pressure. The following results were reported:

|  | Catalyst A | Catalyst B |
| --- | --- | --- |
| Ethylbenzene Conversion (%) | 61 | 63 |
| Ring Loss (%) | 0.03 | 0.15 |
| Ethane:Ethylene Ratio | 78 | 373 |
| Xylenes Loss (%) | 3.9 | 2.3 |

It will be seen that Catalyst B exhibited lower xylene loss and higher ethylene saturation activity (as demonstrated by a higher ethane:ethylene ratio) than Catalyst A. In both cases, the loss of aromatic rings by saturation was negligible.

EXAMPLE 5

ZSM-5 (having a crystal size of about 1 micron), $Al_2O_3$, and tetraammine platinum chloride were extruded to 1/20" cylindrical shaped particles and dried at 250° F. (120° C.) to produce a material with 50:50 by weight ZSM-5:$Al_2O_3$ and 0.1 wt % Pt. This material was then precalcined in nitrogen at 1000° F. (540° C.) for three hours, then exchanged with ammonium nitrate and calcined in air at 1000° F. (540° C.) for 6 hours. Finally, the material was steamed at 900° F. (482° C.) for 3.5 hours to lower the alpha value of the catalyst to 116. The final catalyst had a BHA value of 130 and a platinum dispersion, as measured by hydrogen chemisorption, of 0.2.

We claim:

1. An ethylbenzene conversion catalyst comprising a molecular sieve and a hydrogenation metal, wherein said catalyst exhibits a benzene hydrogenation activity at 100° C. of less than about 100 and a metal dispersion, as measured by hydrogen chemisorption, greater than 0.4 and wherein said molecular sieve has been steamed to an alpha value of less than 400 prior to incorporation of the hydrogenation metal with the molecular sieve.

2. The catalyst of claim 1 wherein said catalyst exhibits a benzene hydrogenation activity at 100° C. of less than about 30 and a metal dispersion, as measured by hydrogen chemisorption, of at least 0.5.

3. The catalyst of claim 1 wherein said hydrogenation metal is palladium.

4. The catalyst of claim 3 wherein said catalyst contains about 0.01 to about 1 wt % of palladium.

5. The catalyst of claim 3 wherein said molecular sieve has been steamed to an alpha value of about 50 to about 250 prior to incorporation of the palladium with the molecular sieve.

6. The catalyst of claim 1 wherein said molecular sieve has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury.

7. The catalyst of claim 1 wherein said molecular sieve has a Constraint Index of about 1 to about 12.

8. The catalyst of claim 1 wherein said molecular sieve is selected from ZSM-5; ZSM-11; ZSM-12; ZSM-22; ZSM-23; ZSM-35; ZSM-48; ZSM-57 and ZSM-58.

9. The catalyst of claim 1 wherein said molecular sieve includes ZSM-5.

* * * * *